United States Patent [19]

Boden et al.

[11] Patent Number: 4,914,082
[45] Date of Patent: Apr. 3, 1990

[54] S(4-HYDROXY-1-ISOPROPYL-4-METHYL-HEXYL) THIOACETATE, ORGANOLEPTIC USES THEREOF AND PROCESS FOR PREPARING SAME

[75] Inventors: Richard M. Boden, Ocean; Joseph A. McGhie, South Orange, both of N.J.

[73] Assignee: International Flavors & Fragrances Inc., New York, N.Y.

[21] Appl. No.: 407,062

[22] Filed: Sep. 14, 1989

Related U.S. Application Data

[62] Division of Ser. No. 273,017, Nov. 18, 1988.

[51] Int. Cl.[4] .................................................. A61K 7/46
[52] U.S. Cl. .................................... 512/7; 252/174.11; 252/8.6
[58] Field of Search ................ 512/7, 26; 252/174.11, 252/8.6

[56] References Cited

U.S. PATENT DOCUMENTS

| | | | |
|---|---|---|---|
| 3,959,396 | 5/1976 | Ochsner et al. | 512/26 |
| 4,311,617 | 1/1982 | Ansari et al. | 512/26 |
| 4,399,062 | 8/1983 | Boden | 512/7 |
| 4,510,319 | 4/1985 | Willis et al. | 512/26 |
| 4,600,576 | 7/1986 | Pittet et al. | 512/7 |

*Primary Examiner*—James H. Reamer
*Attorney, Agent, or Firm*—Arthur L. Liberman

[57] ABSTRACT

Described is the S(4-hydroxy-1-isopropyl-4-methylhexyl) thioacetate having the structure:

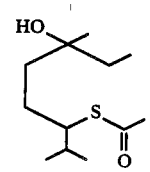

and uses thereof in augmenting or enhancing the aroma of consumable materials including perfume compositions, colognes, perfumed articles and perfumed polymers.

9 Claims, 5 Drawing Sheets

GLC PROFILE FOR EXAMPLE I.
CRUDE

GLC PROFILE FOR FRACTION 4 OF
EXAMPLE I. DISTILLATION.

FIG.3 NMR SPECTRUM FOR EXAMPLE I.

S(4-HYDROXY-1-ISOPROPYL-4-METHYLHEXYL) THIOACETATE, ORGANOLEPTIC USES THEREOF AND PROCESS FOR PREPARING SAME

This is a divisional of application Ser. No. 273,017, filed 11/18/88.

BACKGROUND OF THE INVENTION

Described is the S(4-hydroxy-1-isopropyl-4-methylhexyl) thioacetate defined according to the structure:

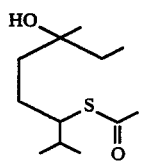

and uses thereof in augmenting or enhancing the aroma of perfume compositions, colognes, perfumed articles and perfumed polymers.

There has been considerable work performed relating to substances which can be used to impart (or alter, modify or enhance) fragrances and aromas to (or in) perfume compositions, colognes and perfumed articles. These substances are used to diminish the use of natural materials some of which may be in short supply and/or to provide more uniform properties in the finished product.

Powerful, long-lasting green, floral and rose aromas are highly desirable for many types of perfume compositions, perfumes and perfumed articles, particularly herbal fragrances and herbal fragranced soaps and detergents.

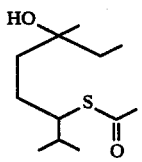

(Conditions: SE-30 column programmed at 100°-220° C. at 8° C. per minute)

Figure 2:
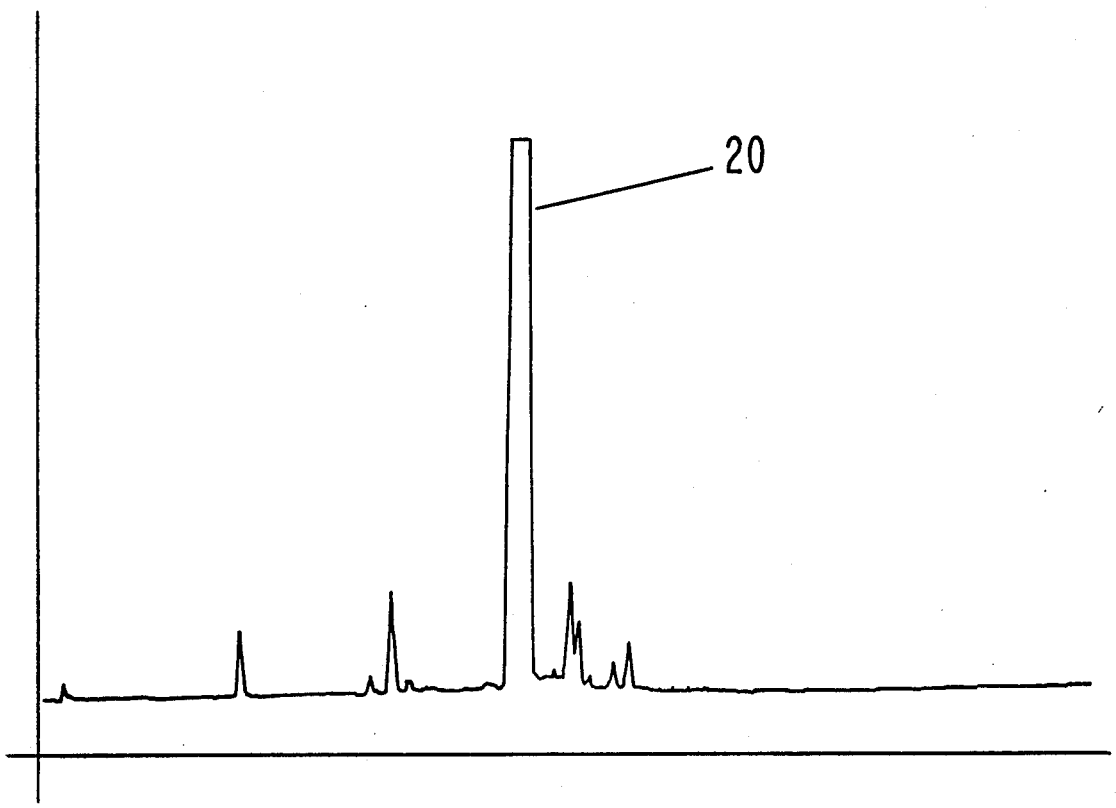

FIG. 2 is the GLC profile for fraction 4 of the distillation of the reaction product of Example I containing the compound having the structure:

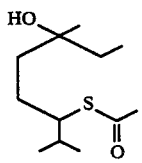

(Conditions: SE-30 column programmed at 100°-220° C. at 16° C. per minute).

Figure 3:
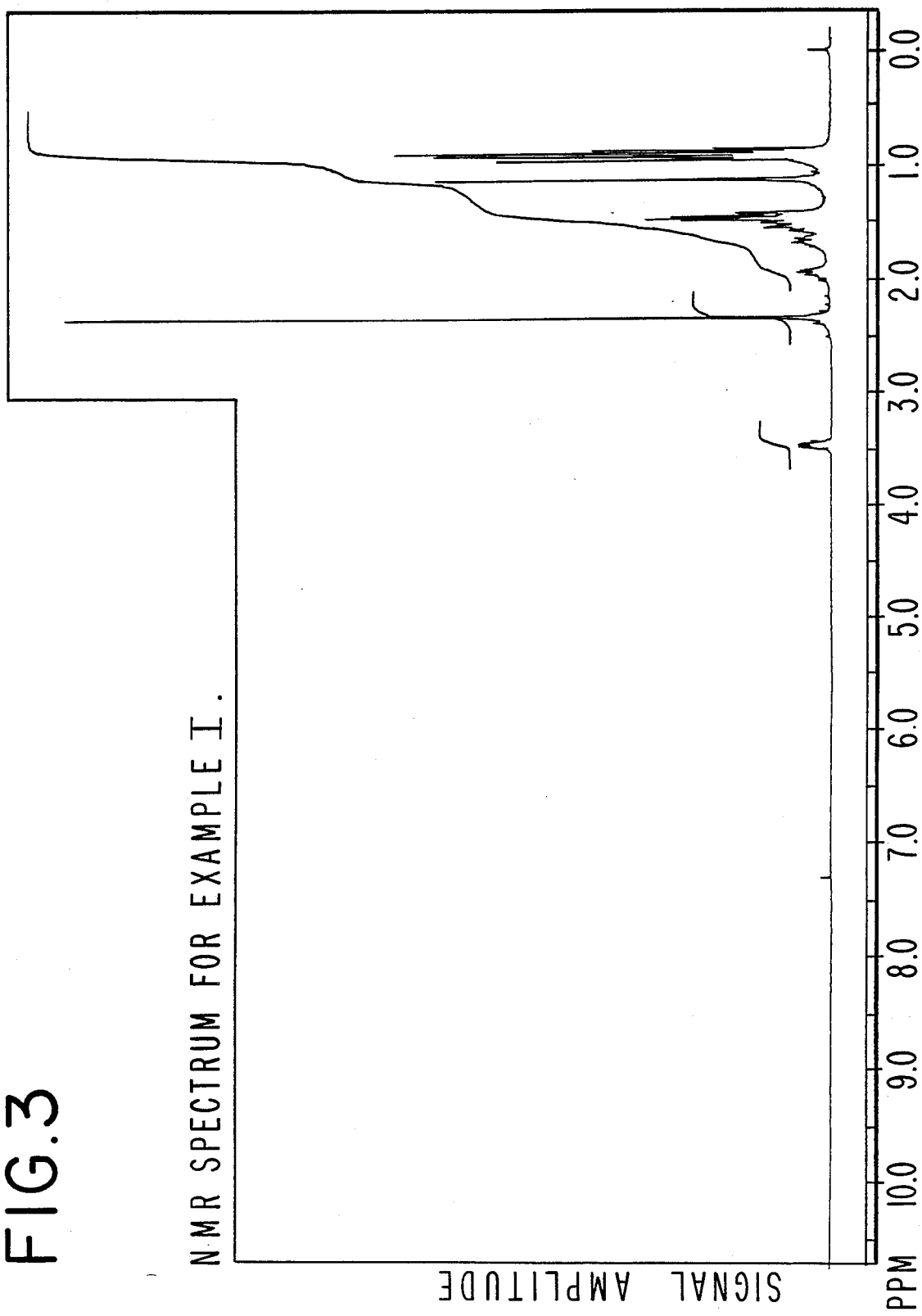

FIG. 3 is the NMR spectrum for the compound having the structure:

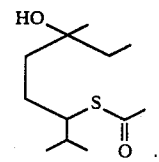

Figure 4:
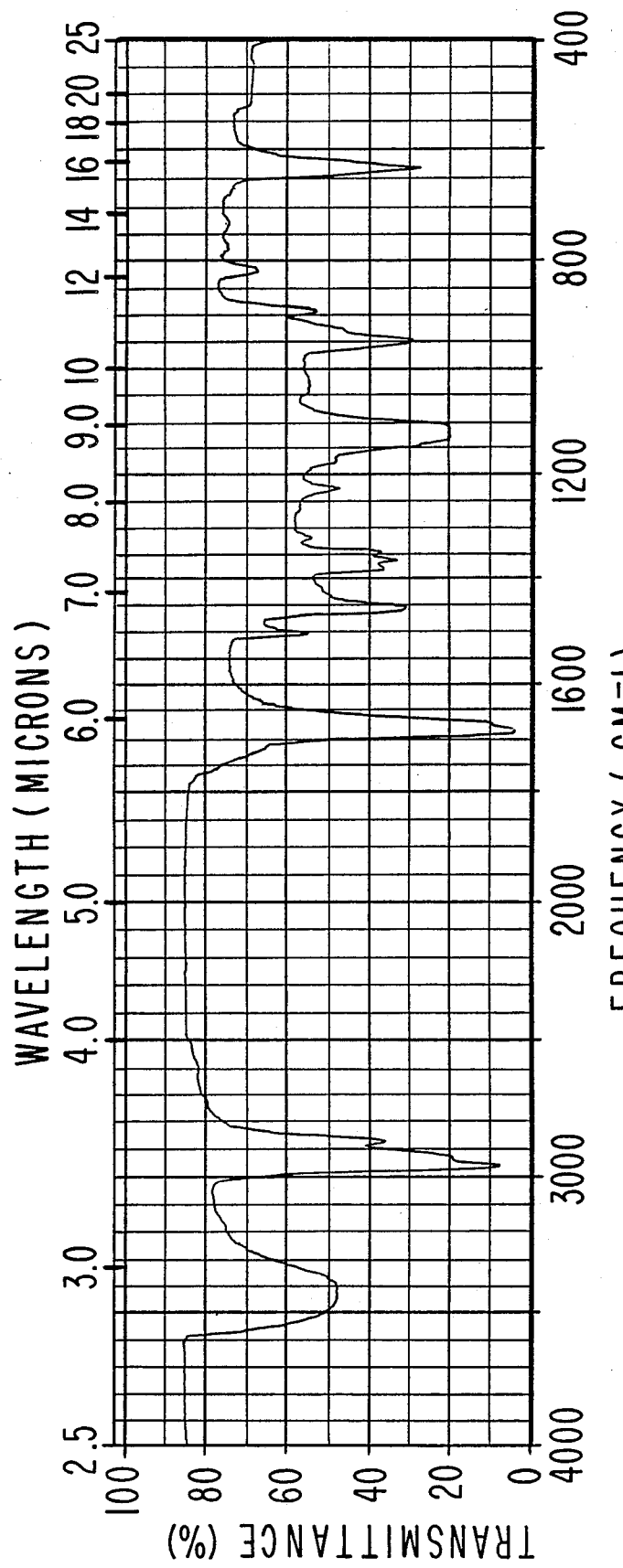

FIG. 4 is the infra-red spectrum for the compound having the structure:

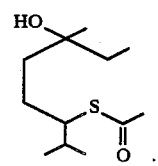

Figure 5:
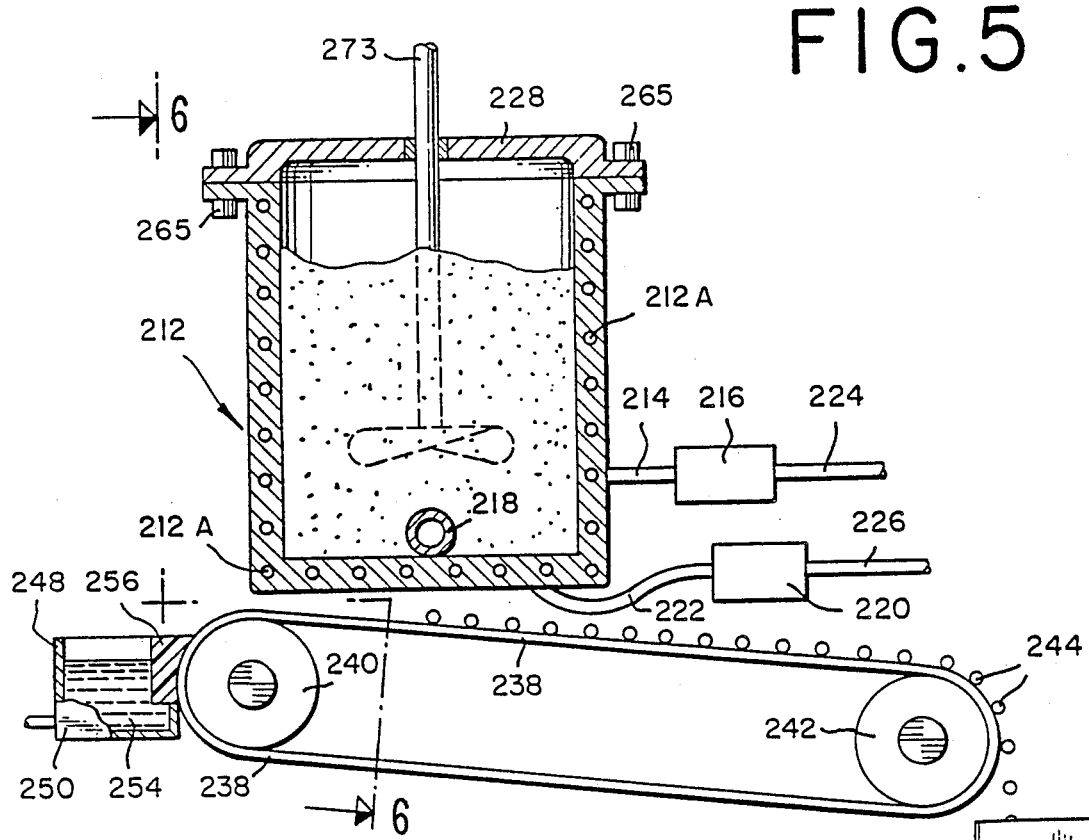

FIG. 5 is a cut-away side elevation view of apparatus used in preparing the fragrance containing polymers of our invention.

Figure 6:
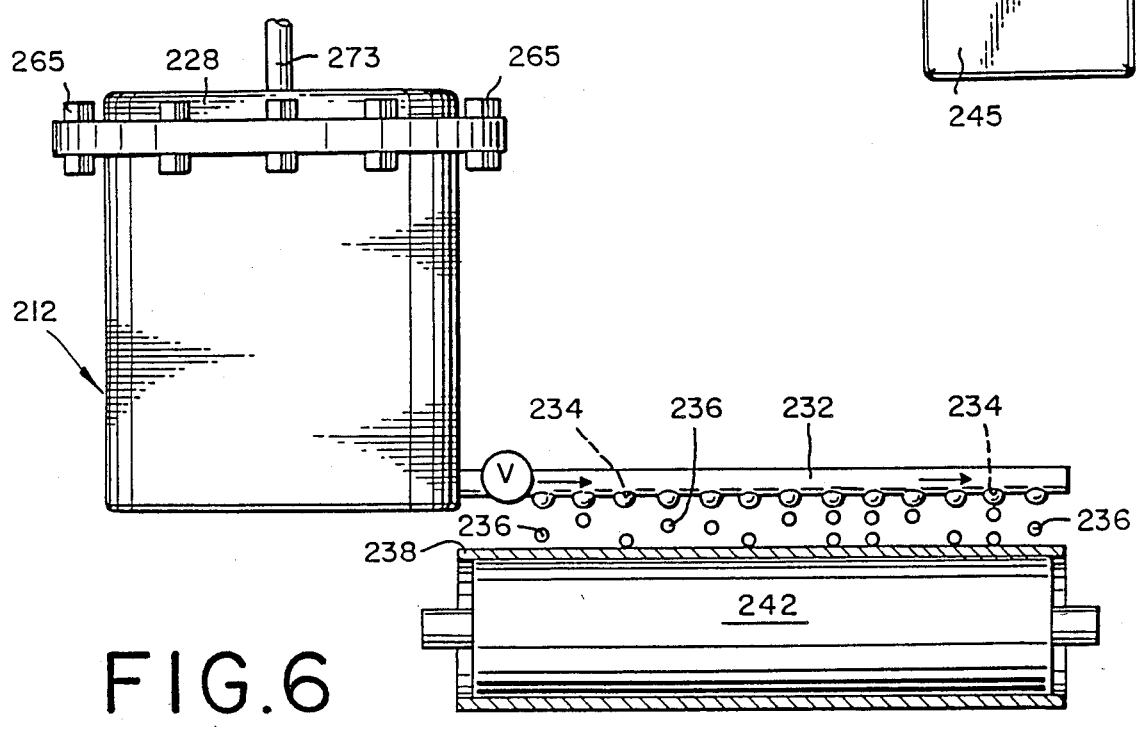

FIG. 6 is a cross sectional view taken along lines 6—6 of FIG. 5.

DETAILED DESCRIPTION OF THE DRAWINGS

Figure 1:
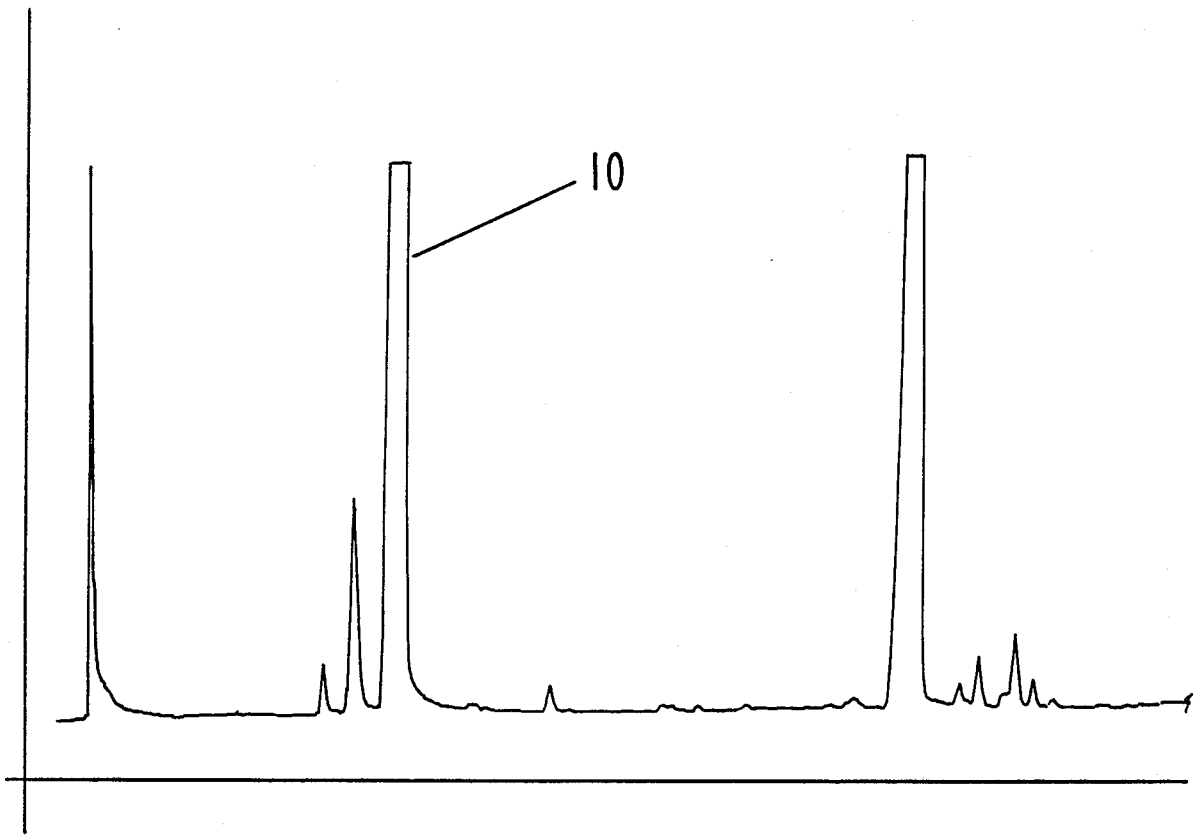
FIG. 1 is the GLC profile for the crude reaction product of Example I containing the compound having the structure.

FIG. 1 is the GLC profile for the crude reaction product of Example I. The peak indicated by reference numeral 10 is the peak for the compound having the structure:

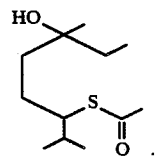

FIG. 2 is the GLC profile for fraction 4 of the distillation of the reaction product of Example I. The peak indicated by reference numeral 20 is the peak for the compound having the structure:

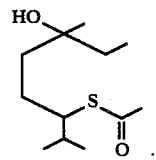

Referring to FIGS. 5 and 6, a thermoplastic polymer, e.g., polyethylene is heated to about 220°-250° C. in a container 212 for the kind illustrated in FIGS. 5 and 6. A formulation containing the compound having the structure:

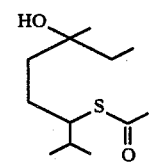

is then quickly added to the liquified thermoplastic polymer. The lid 228 is put in place and the agitating means 273 is actuated. The temperature is maintained at about 225° F. and the mixing is continued for about 5–15 minutes. The valve "V" is then opened to allow flow of the molten thermoplastic polymer enriched with the fragrance containing the S(4-hydroxy-1-isopropyl-4-methylhexyl) thioacetate to exit through the orifices 234. The liquid falling through the orifices 234 solidifies almost instantaneously upon impact with the moving cooled conveyor 238. The thermoplastic polymer beads or pellets 224 having pronounced aromas which are aesthetically pleasing are thus formed.

The conveyor 238 is moved using conveyor rollers 240 and 242. The vessel 212 is heated using heating coils 212A using power imput supplies indicated by reference numerals 214, 216, 224, 222, 220 and 226. The solidified beads containing fragrance containing the S(4-hydroxy-1-isopropyl-4-methylhexyl) thioacetate of our invention are indicated by 244 traveling into container 245 where they are used for subsequent processing. The conveyor is cooled using a cooling device indicated by reference numerals 248, 256, 215 and 254.

THE INVENTION

The invention relates to the S(4-hydroxy-1-isopropyl-4-methylhexyl) thioacetate defined according to the structure:

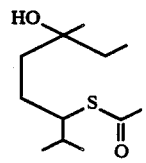

as well as uses thereof in augmenting or enhancing the aroma of consumable materials including perfumes, colognes and perfumed articles. This invention also relates to a process for preparing the S(4-hydroxy-1-isopropyl-4-methylhexyl) thioacetate having the structure:

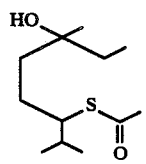

by reacting thioacetic acid having the structure:

with dihydrolinalool having the structure:

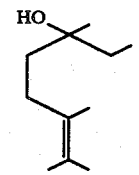

according to the reaction:

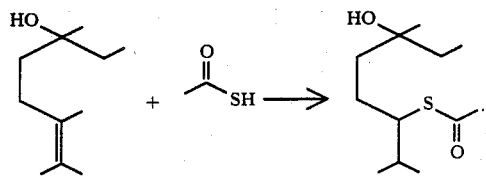

The reaction is carried out at a temperature in the range of from about 65° C. up to about 95° C. for a period of time of from about one hour up to about five hours. The mole ratio of dihydrolinalool having the structure:

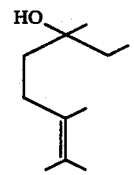

to thioacetic acid having the structure:

may range from about 0.5:1.5 up to about 1.5:0.5 with a preferred mole ratio of about 3.0 moles dihydrolinalool to 2.5 moles thioacetic acid.

The compound having the structure:

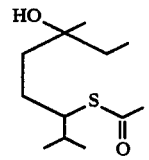

has a green, floral and rose aroma profile.

The S(4-hydroxy-1-isopropyl-4-methylhexyl) thioacetate having the structure:

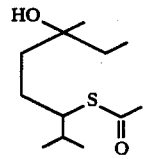

is useful as an olfactory agent and can be incorporated into a wide variety of compositions each of which will be enhanced or augmented by its green, floral and rose nuances.

The S(4-hydroxy-1-isopropyl-4-methylhexyl) thioacetate can be added to perfume compositions as a pure compound or can be added to mixtures of materials in fragrance imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the S(4-hydroxy-1-isopropyl-4- methylhexyl) thioacetate of our invention is useful as an olfactory agent and fragrance.

The term "perfume composition" is used herein to mean a mixture of compounds including, for example, natural essential oils, synthetic essential oils, alcohols, aldehydes, ketones, esters (other than the ester of our invention), lactones, nitriles and frequently hydrocarbons which are admixed so that the combined odors of the individual components produce a pleasant or desired fragrance. Such perfume compositions usually contain (a) the main note or "bouquet" or foundation stone of the composition, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials. Such perfume compositions of our invention ca be used in conjunction with carriers, vehicles, solvents, dispersants, emulsifiers, surface active agents, aerosol propellants and the like.

In perfume compositions, the olfactory components contribute their particular olfactory characteristics but the overall effect of the perfume composition will be the sum of the effect of each ingredient. Thus, the S(4-hydroxy-1-isopropyl-4-methylhexyl) thioacetate of our invention having the structure:

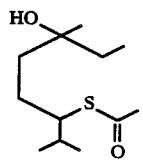

can be used to alter, augment, modify or enhance the aroma characteristics of a perfume composition or a perfumed article, for example, by highlighting or moderating the olfactory reaction contributed by another ingredient of the composition.

The amount of the S(4-hydroxy-1-isopropyl-4-methylhexyl) thioacetate of our invention having the structure:

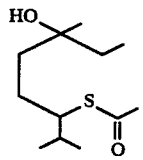

which will be effective in perfume compositions depends upon many factors including the other ingredients, the amounts and the effects which are desired. It has been found that perfume compositions containing as much as 40% or as little as 0.005% by weight of the mixtures or the S(4-hydroxy-1-isopropyl-4-methylhexyl) thioacetate of this invention, or even less, can be used to impart a powerful, long-lasting, stable, green, floral and rose aroma profile to soaps, cosmetics and other products. The amount will depend upon considerations of cost, nature of the end product, the effect desired in the finished product and particular fragrance sought.

The S(4-hydroxy-1-isopropyl-4-methylhexyl) thioacetate of our invention having the structure:

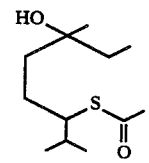

as disclosed herein can be used alone in a fragrance modifying composition or in a perfume composition as an olfactory component in detergents (e.g., anionic, cationic, nonionic or zwitterionic solid or liquid detergents) and soaps; space deodorants; perfumed plastics; perfume compositions; colognes; bath preparations such as both oils, bath salts; hair preparations such as lacquers, brilliantines, pomades and shampoos; fabric softener compositions, fabric softener articles such as BOUNCE ® (manufactured by the Procter & Gamble Company of Cincinnati, Ohio), cosmetic preparations such as creams, powders, deodorants, hand lotions, sun screens, powders such as talcs, dusting powders, face powders and the like. When the S(4-hydroxy-1-isopropyl-4-methylhexyl) thioacetate of our invention having the structure:

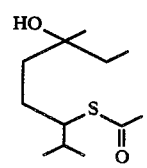

is used in perfumed articles such as the foregoing, it can be used in amounts of 0.01% or lower and generally it is preferred not to use more than about 2% in the finished perfumed article since the use of too much will tend to unbalance the total aroma and will needlessly raise the cost of the article. Thus, in summary, in perfumed articles, the S(4-hydroxy-1-isopropyl-4-methylhexyl) thioacetate of our invention having the structure:

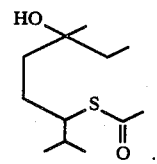

may be used in the range of from about 0.01% up to about 2.0%.

The following Example I is given to illustrate a method for preparing the S(4-hydroxy-1-isopropyl-4-methylhexyl) thioacetate of our invention having the structure:

Examples following Example I illustrate methods for utilizing the S(4-hydroxy-1-isopropyl-4-methylhexyl)

thioacetate of our invention for its organoleptic properties.

It will be understood that these examples are illustrative and the invention is not to be considered as restricted thereto except as indicated in the appended claims.

EXAMPLE I

Preparation of
S(4-Hydroxy-1-Isopropyl-4Methylhexyl) Thioacetate

Reaction:

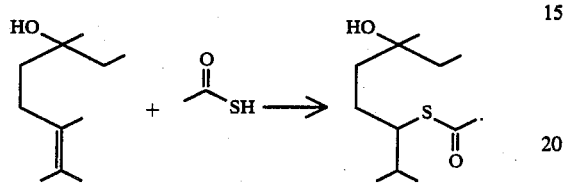

Into a 1 liter reaction vessel equipped with stirrer, thermometer, reflux condenser and heating mantle is placed 468.0 grams (3.0 moles) of dihydrolinalool having the structure:

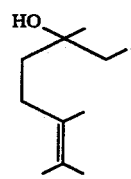

The dihydrolinalool is heated to 65° C. with stirring. While maintaining the dihydrolinalool at 65° C., dropwise over a period of one hour, thioacetic acid having the structure:

is added to the reaction mass. After addition of the thioacetic acid, the reaction mass is maintained at 65°–70° C. for a period of one hour. The reaction mass is then heated to 85°–90° C. for a period of one hour with stirring.

The reaction mass is then cooled and washed with two 200 cc portions of 20% aqueous sodium hydroxide.

The resulting product is distilled on a 4" splash column yielding the following fractions:

| Fraction No. | Vapor Temp. (C) | Liquid Temp. (C) | Vacuum mm/Hg. Pressure | Weight of Fraction |
|---|---|---|---|---|
| 1 | 75/92 | 80/90 | 3.8/3.8 | 200.0 |
| 2 | 98 | 105 | 3.5 | 200.0 |
| 3 | 125 | 145 | 3.5 | 41.0 |
| 4 | 150 | 220 | 3.5 | 280.0 |

The resulting product has the structure:

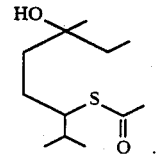

FIG. 1 is the GLC profile for the crude reaction product (Conditions: SE-30 column programmed at 100°–220° C. at 8° C. per minute). The peak indicated by reference numeral 10 is the peak for the compound having the structure:

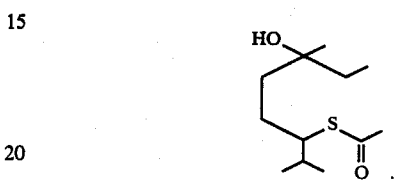

FIG. 2 is the GLC profile for fraction 4 of the distillation product of the reaction product of Example I. The peak indicated by reference numeral 20 is the peak for the compound having the structure:

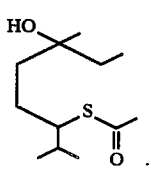

FIG. 3 is the NMR spectrum for the compound having the structure:

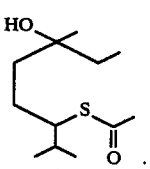

FIG. 4 is the infra-red spectrum for the compound having the structure:

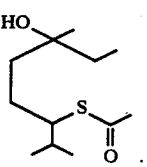

EXAMPLE II(A)

Impregnated Plastics and Air Fresheners

Scented polyethylene pellets having a pronounced green, floral and rose aroma are prepared as follows:

75 Pounds of polyethylene having a melting point of about 220° F. is heated to about 230° F. in a container of the kind illustrated in FIGS. 5 and 6. 12.5 Pounds of S(4-hydroxy-1-isopropyl-4-methylhexyl) thioacetate prepared according to Example I are then quickly added to the liquefied polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the S(4-hydroxy-1-isopropyl-4-methylhexyl) thioacetate-containing material through the orifices 234 whereby such material exits through orifices 234. The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼" in width×3" in length and employed in standard air freshening apparatus.

On operation of the standard air freshening apparatus as a room air freshener, after 4 minutes, the room has an aesthetically pleasing aroma as set forth, supra.

EXAMPLE II(B)

Treated Plastics and Air Freshener

100 Pounds of polypropylene are heated to about 300° F. 15 Pounds of S(4-hydroxy-1-isopropyl-4-methylhexyl) thioacetate prepared according to Example I are added to the liquefied polypropylene. The procedure is carried out in the apparatus shown in FIGS. 5 and 6. After mixing for about 8 minutes, the valve "V" is opened to allow the exit of polypropylene mixture which has been treated with the S(4-hydroxy-1-isopropyl-4-methylhexyl) thioacetate, whereby solid pellets having pronounced aromas described as green, floral and rose are formed on the conveyor. The pellets thus obtained are then admixed with about 20 times their weight of unscented polypropylene ad untreated polypropylene and the mixture is heated and molded into "spaghetti" tows. The "spaghetti" tows are cut into small cylinders approximately 0.1 inches in length×0.2 inches in diameter. The cylinders have strong and pleasant aromas as described, supra.

The cylinders are used in standard air freshening apparatus to produce aesthetically pleasing aromas as set forth, supra with no foul odors in environments surrounding the air freshener apparatus.

A portion of the cylinders are ground into small particles to be used in the deodorant stick of Example II(C), infra.

EXAMPLE II(C)
DEODORANT STICK

A deodorant stick composition is prepared containing the following materials

| Ingredients | Parts by Weight |
|---|---|
| Propylene Glycol | 65.00 |
| Sodium stearate | 7.00 |
| Distilled water | 23.75 |
| IRGSAN ® DP-300 (2,4,4-trichloro-2'-hydroxy diphenyl ether, manufactured by the Ciba Geigy Chemical Company of Hastings On Hudson, New York) | 0.25 |
| Ground polymer containing fragrance produced according to Example II(B), supra. | 4.00 |

The ingredients are combined without the ground polymer and heated to 75° C. These ingredients are mixed and continued to be heated until the sodium stearate has dissolved. The resulting mixture is cooled to 40° C. and the ground fragrance-containing polymer is added and mixed at 40° C. until the suspension is formed. The resulting suspension is cooled and formed into sticks and the deodorant sticks exhibit a pleasant, fresh, green, floral, rose aroma when utilized in the axillary areas of a human being.

EXAMPLE III

Herbal Perfume Formulation

The following mixtures are prepared:

| | Parts by Weight | |
|---|---|---|
| Ingredients | Example III(A) | Example III(B) |
| Oakmoss absolute (50% in diethyl phthalate) | 20 | 20 |
| Alpha-methyl-3,4-methylene-dioxyhydrocinnamic aldehyde | 10 | 10 |
| Methyl dihydrojasmonate | 100 | 100 |
| Coumarin | 20 | 20 |
| Musk ketone | 80 | 80 |
| Isocyclocitral (10% in diethyl phthalate) | 10 | 10 |
| Galbanum oil (10% in diethyl phthalate) | 6 | 6 |
| Rosemary oil | 10 | 10 |
| Pine needle oil | 60 | 60 |
| Fir balsam absolute (10% in diethyl phthalate) | 10 | 10 |
| Bergamot oil | 60 | 60 |
| Lemon oil | 14 | 14 |
| Benzyl acetate | 468 | 468 |
| Linalool | 80 | 80 |
| Indole (10% in diethyl phthalate) | 6 | 6 |
| Undecalactone (10% in diethyl phthalate) | 12 | 12 |
| 2-Methyl-4-phenyl-1-pentanol prepared according to U.S. Letters Patent 4,632,831 | 12 | 0 |
| 2-Methyl-4-phenyl-1-pentanol acetate prepared according to U.S. Letters Patent 4,632,831 | 0 | 20 |
| S(4-hydroxy-1-isopropyl-4-methylhexyl) thioacetate prepared according to Example I, supra | 10 | 20 |

The addition to this herbal formulation of the S(4-hydroxy-1-isopropyl-4-methylhexyl) thioacetate imparts to this herbal formulations excellent green, floral and rose undertones. Accordingly, the formulations of Examples III(A) and III(B) can be described as "herbaceous, with green, floral and rose undertones".

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| S(4-hydroxy-1-isopropyl-4-methylhexyl)thioacetate having the structure: | A green, floral, rose aroma profile. |

TABLE I-continued

| Substance | Aroma Description |
|---|---|
| 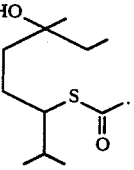 | |
| Perfume composition of Example III(A). | A herbaceous aroma with green, floral and rose undertones. |
| Perfume composition of Example III(B). | A herbaceous aroma with green, floral and rose undertones. |

EXAMPLE V

Perfumed Liquid Detergents

Concentrated liquid detergents (Lysine salt of n-dodecylbenzene sulfonic acid as more specifically described in U.S. Pat. No. 3,948,818 issued Apr. 6, 1976 incorporated by reference herein) with aroma nuances as set forth in Table I of Example IV are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation of Soap Compositions

One hundred grams of soap chips (per sample) (IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table I of Example IV.

EXAMPLE VIII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "NEODOL ® 45-11 (a $C_{14}$—$C_{15}$ alcohol ethoxylanted with 11 moles of ethylene oxide. | 12 |
| Sodium carbonate | 55 |
| Sodium citrate | 20 |
| Sodium sulfate, water brighteners. | q.s. |

This detergent is a phosphate-free detergent. Samples of 100 grams each of this detergent are admixed with 0.10, 0.15, 0.20 and 0.25 grams of each of the substances as set forth in Table of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabic softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and pH3. An outer coating having the following formulation (m.p. about 150° F.):
57%: $C_{20\text{-}22}$ HAPS 22%: isopropyl alcohol 20%: antistatic agent 1%: of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example IV, supra.

EXAMPLE X

Hair Spray Formulations

The following hair spray formulation is prepared by first dissolving PVP/VA E-b 735 copolymer manufactured by the GAF Corporation of 140 West 51st Street, New York, New York, in 91.62 grams of 95% food grade ethanol. 8.0 Grams of the polymer is dissolved in the alcohol. The following ingredients are added to the PVP/VA alcoholic solution:

| | Weight Percent |
|---|---|
| Dioctyl sebacate | 0.05 |
| Benzyl alcohol | 0.10 |
| Dow Corning 473 fluid | 0.10 |
| (prepared by the Dow Corning | 0.10 |

| | Weight Percent |
|---|---|
| Corporation) | |
| Tween 20 surfactant (prepared by ICI America Corporation) | 0.03 |
| One of the perfumery substances as set forth in Table I of Example IV, supra. | 0.10 |

The perfuming substances as set forth in Table I of Example IV add aroma characteristics as set forth in Table I of Example IV which are rather intense and aesthetically pleasing to the users of the soft-feel, good hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, New York)(5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. A process for augmenting or enhancing the aroma of a consumable material selected from the group consisting of perfume compositions, colognes and perfumed articles comprising the step of intimately admixing with said consumable material, an aroma augmenting or enhancing quantity of s(4-hydroxy-1-isopropyl-4-methylhexyl) thioacetate having the structure:

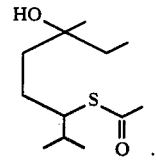

2. The process of claim 1 wherein the consumable material is a polymer.
3. The process of claim 1 wherein the consumable material is a perfume composition or cologne.
4. The process of claim 1 wherein the consumable material is a perfumed article and the perfumed article is a solid or liquid anionic, cationic, nonionic or zwitterionic detergent.
5. The process of claim 1 wherein the consumable material is a perfumed article and the perfumed article is a fabric composition or fabric softener article.
6. The process of claim 1 wherein the consumable material is a perfumed article and the perfumed article is a deodorant stick.
7. The process of claim 1 wherein the consumable material is a perfumed article and the perfumed article is cosmetic powder.
8. A perfume composition comprising a perfume base and intimately admixed therewith the compound having the structure:

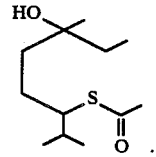

9. A detergent composition of matter comprising a detergent base and intimately admixed therewith the compound having the structure:

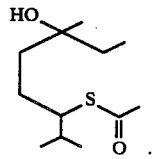

* * * * *